United States Patent [19]
Selitrennikoff et al.

[11] Patent Number: 5,912,153
[45] Date of Patent: Jun. 15, 1999

[54] (1,3) β-GLUCAN SYNTHASE GENES AND INDUCIBLE INHIBITION OF FUNGAL GROWTH USING THE ANTISENSE CONSTRUCTS DERIVED THEREFROM

[76] Inventors: Claude P. Selitrennikoff, 264 Ponderosa Place, Evergreen, Colo. 80439; Carol S. Enderlin, 1313 Jasmine St., Denver, Colo. 80220

[21] Appl. No.: 08/579,777

[22] Filed: Dec. 28, 1995

Related U.S. Application Data

[63] Continuation-in-part of application No. 08/155,004, Nov. 18, 1993, abandoned.

[51] Int. Cl.[6] .............................. C12N 1/21; C12N 15/54; C12N 15/63; C12P 21/02
[52] U.S. Cl. .................... 435/193; 435/91.1; 435/91.41; 435/252.3; 435/320.1; 435/325; 536/23.2
[58] Field of Search ........................ 536/23.2; 435/91.1, 435/91.41, 320.1, 325, 252.3, 193

[56] References Cited

U.S. PATENT DOCUMENTS

| | | | |
|---|---|---|---|
| 4,873,196 | 10/1989 | Selitrennikoff | 435/254.4 |
| 5,194,600 | 3/1993 | Bussey et al. | 536/23.74 |
| 5,484,724 | 1/1996 | El-Sherbeini et al. | 435/193 |

OTHER PUBLICATIONS

Enderlin et al., Proc. Natl. Acad. Sci. USA 91:9500–9504, 1994

Taft et al., J. Antibiotics 41:697–701, 1988.

Taft et al., J. Enzyme Inhib. 5:41–49, 1991.

*Primary Examiner*—Eric Grimes
*Attorney, Agent, or Firm*—Davis, Graham & Stubbs LLP

[57] ABSTRACT

A (1,3)β-glucan synthase mutant useful in the research and development of anti-fungal drugs. A key step in fungal wall assembly, hyphal growth and infection is the synthesis of (1,3)β-linked glucan. Because β-glucan is not made by humans, (1,3)β-glucan synthase is an attractive target for development of new antifungal antibiotics. A (1,3)β-glucan synthase gene has been cloned and the cDNA sequence and polypeptide amino acid sequence of the gene has been established.

16 Claims, 5 Drawing Sheets ers of use Amphotericin B (a polyene) is still the drug of
(1,3) β-GLUCAN SYNTHASE GENES AND INDUCIBLE INHIBITION OF FUNGAL GROWTH USING THE ANTISENSE CONSTRUCTS DERIVED THEREFROM

CROSS-REFERENCE TO RELATED APPLICATIONS

This application is a continuation-in-part of U.S. patent application Ser. No. 08/155,004 filed Nov. 18, 1993, now abandoned.

FIELD OF INVENTION

The present invention relates to (1,3)β-glucan synthase, and more specifically to the characterization and reproduction of a (1,3)β-glucan synthase gene and antisense constructs useful in the development of new antifungal antibiotics.

BACKGROUND OF THE INVENTION

Human fungal infections are serious and often life-threatening, particularly for immunocompromised patients. Immunocompromised patients provide a great challenge to modern health care delivery. For example, the mean survival time of AIDS patients with cryptococcal infections is 8.4 months (NIH meeting; Medical Mycology, June, 1993). These infections are often the result of opportunistic fungi that are usually asymptomatic commensals, as described by M. Shepard; R. Poulter & P. Sullivan: "Candida albicans: Biology, Genetics, and Pathogenicity", Ann. Rev. Microbiol. Vol. 39 (1985) pp. 579–614.

Immune deficiencies, which are often caused by antineoplastic chemotherapy, organ transplants, congenital defects, leukemia, Hodgkin's disease, diabetes, and HIV infection render an immunocompromised host susceptible to a large number and variety of neoplastic, protozoal, viral, bacterial, and fungal diseases. Of these, bacterial, viral and fungal infections result in the greatest mortality. During the last three decades there has been a dramatic increase in the frequency of fungal infections, especially disseminated systemic mycoses in immunodeficient hosts. As previously mentioned, mycoses in compromised hosts are mainly the result of opportunistic infections by organisms that are normally harmless asymptomatic commensals, which can be, under certain conditions, pathogenic. Fungi of particular importance include: Cryptococcus, Candida, Coccidioides, Histoplasma, Sporothrix, and Aspergillus; of these Candida infections are the most common. Candidiasis has a large number of clinical presentations ranging from cutaneous to disseminated systemic infections and includes oral thrush, bronchitis, meningitis, septicemia, asthma, gastritis, uveitis and endocarditis. Additionally, Pneumocystis carnii is the leading cause of deaths in AIDS patients and recent data based on 16S-like RNA sequence analysis reveal that Pneumocystis carnii is related to fungi.

It is known that the treatment of mycotic infections is difficult due to a lack of effective antifungal antibiotics. See, for example, Ringel, S.; "New Antifungal Agents for the Systemic Mycoses", Mycopath. Vol. 109 (1990) pp. 75–87; Walsh, T.; P. Jarosinski & R. Fromtherling: "Increasing Usage of Systemic Antifungal Agents", Diagn. Microbial. Infections, Vol. 13, (1990) pp. 37–40; Medoff, G.; J Brajtburg, J. Boland & G. Kobayashi: "Antifungal Agents Useful in Therapy of Systemic Fungal Infections", Ann. Rev. Pharm. Tox. Vol. 23 (1983) pp. 303–330. Even after 29 years of use Amphotericin B (a polyene) is still the drug of choice to treat systemic fungal infections. See Ryley, J.; R. Wilson, M. Gravestock & P. Poyser: "Experimental Approaches to Antifungal Chemotherapy", Adv. Pharm. Chemother. Vol. 18 (1981) pp.49–177; Gallis, H.; R.Drew & W. Pickard: "30 Years of Clinical Experience, Rev. Inf. Dis. Vol. 12 (1990) pp. 308–329.

The apparent mode of action of Amphotericin B (AmB) is to complex with membrane sterols, resulting in membrane distortion and leakage of intracellular contents. In addition, AmB is an immunostimulant. However, AmB is very toxic to human cells and AmB therapy is fraught with side effects which include renal dysfunction, fever, chills, hypotension and even cardiac failure. In spite of toxicity and problems with formulation (AmB is not orally active but must be administered intravenously), AmB is the most used systemic antifungal agent.

Other treatment options include imidazoles (for example Ketoconazole, miconazole), which inhibit fungal growth by inhibiting the C-14 demethylation step in sterol biosynthesis. Although are orally active, they are not recommended for use in the treatment of systemic infections in immunocompromised patients. Ryley, J.; R. Wilson, M. Gravestock & P. Poyser: "Experimental Approaches to Antifungal Chemotherapy", Adv. Pharm. Chemother. Vol. 18 (1981) pp.49–177. Still other antifungal agents exist, for example flucytosine, Cilofungin, Papulacandin B, Aculeacin A, yet they are limited by either narrow spectrum of activity or by toxicity or both. The limitations of the prior art indicate a need for new, effective antifungal antibiotics that eliminate the side effects of those antibiotics available today.

The key to developing effective antifungal therapeutics lies in targeting fungal-specific enzymes or molecules. One such target, perhaps the most unique, is the fungal cell wall. In studying fungal cells, it is noted that the most striking difference between fungal cells and human cells is that fungal cells are encased in a wall which protects them from an osmotically and immunologically hostile external environment. The fungal cell wall relays signals for invasion and infection of a likely plant, animal or human host. The cell wall of fungi has a complex composition and structure and has been the subject of several reviews. See, for example: Ruiz-Herrera, J.: "Fungal Cell Wall: Structure, Synthesis and Assembly, CRC Press. Fl., 1992; Gooday, G & N. Gow: "Enzymology of Tip Growth in Fungi. Tip Growth in Plant and Fungal Cells", I. B. Health, Ed. Acad. Press, 1990; Wessels, J. G. H.: "Wall Growth, Protein Excretion and Morphogenesis in Fungi, New Phytol. Vol. 123 (1993) pp. 397–413.

In general, human pathogenic fungi, in both yeast and filamentous forms, contain chitin (GlcNAc polymer), (1,3) β-glucan, other glucans (some even contain cellulose), peptides, lipids, and a small amount of unknown material. Fungal cell walls, when fixed and viewed by standard electron microscopic techniques, appear trilayered and roughly 150–250 nm thick. For filamentous fungi, growth and cell-wall assembly occur only at each hyphal apex. Ruiz-Herrera,J. L. "Fungal Cell Wall: Structure, Synthesis and Assembly", CRC Press Fl., 1992; Wessels, J. G. H.: "Wall Growth, Protein Excretion and Morphogenesis in Fungi", New Phytol. Vol. 123 (1993) pp. 397–413. Normal cell-wall assembly is essential for growth and viability of a large number of fungi. This proposition has been convincingly shown using cell-wall acting drugs and by the analysis of mutants defective in key wall-assembly steps. See Scott, W. A.: "Biochemical Genetics of Morphogenesis in Neurospora", Ann. Review Microbiol. Vol. 30 (1976) pp. 85–104; Shaw, J.;P. Mol, B. Bowers, D. Silverman, M.

Vadiviesco, A, Duran & E. Cabib: "The Function of Chitin Synthases 2 and 3 in the Saccharomyces cerevisiae Cell Cycle", J. Cell Biol. Vol. 114 (1991) pp. 111–123.

There are a large number of single-gene mutants of several fungi that result in abnormal cell-wall assembly and morphogenesis. For example, in the filamentous Ascomycete, *Neurospora crassa*, there are over 150 single-gene morphological mutants. However, dissecting cell-wall assembly by examining morphological mutants has not proven feasible for it is likely that many of these mutants produce defective enzymes involved in intermediary metabolism. As an example, col-1 is glc-6-P dehydrogenase defective. It has proven nearly impossible to relate directly a deficit in intermediary metabolism to cell-wall assembly. It appears that subtle changes in intracellular metabolite concentrations have dramatic effects on wall assembly and resulting hyphal morphology.

Thus far only three enzyme activities have unequivocally been shown to be directly involved in and essential for cell-wall assembly, namely chitin synthase, $(1,6)\beta$-glucan synthase and $(1,3)\beta$-glucan synthase. See Taft, C. & C. Selitrennikoff: "LY121019 Inhibits Neurospora crassa growth and $(1,3)\beta$-D-glucan synthase. J. Antibiotics, Vol. 41 (1988) pp. 697–701; Romer T. & H. Bussey: "Yeast $\beta$-glucan synthase: KRE6 Encodes a Predicted Type Membrane Protein Required for Glucan Synthase in Vivo and for Glucan Synthase Activity in Vitro", Proc. Natl. Acad. Sci. USA vol. 88 (1991) pp. 11295–11299; Roemer, T.; S. Delaney & H. Bussey: "SKN 1 and KRE6 Define a Pair of Functional Homologs Encoding Punative Membrane Proteins Involved in $\beta$-Glucan Synthesis", Molec. Cell. Biol. Vol. 13 (1993) pp. 4039–4048. Since mammalian cells lack chitin, $(1,6)\beta$-glucan synthase and $(1,3)\beta$-glucan, the fungal pathways for their syntheses are attractive targets for antifungal drugs. Chitin synthase as a target for antifungal drugs has been reviewed. Further, the showing that *Pneumocystis carinli* pneumonia was treated successfully with $(1,3)\beta$-glucan synthase inhibitors has greatly stimulated interest in the search for new enzyme inhibitors. See Schmatz, D. et al. "Treatment of Pneumocystis carnii Pneumonia with $(1,3)\beta$-glucan Synthase Inhibitors", Proc. Natl. Acad. Sci. USA Vol. 87 (1990) pp. 4039–4048.

To date, all the information available shows that $(1,3)\beta$-glucan synthase is the important enzyme activity for fungal cell-wall and development. It is shown in the prior art that $(1,3)\beta$-glucan synthase activity is required for normal cell-wall assembly, growth, and development for a large number of fungi, including species of Candida, Aspergillus, and Neurospora. See Wessels, J. G. H.: "Wall Growth, Protein Excretion and Morphogenesis in Fungi, New Phytol. Vol. 123 (1993) pp.397–413; Gorgee, R.: D. Zeckner, L. Ellis, A. Thakkar & L. Howard: "In vitro and in vivo anti-Candida Activity and Toxicology of LY121019", J. Antibiotics, Vol. 37 (1984) pp. 1054–1065; Bozzola, J.; R. Mehta, L. Nisbet & J. Valenta: "The Effect of Aculeacin A and Papulacandin B on Morphology and Cell Wall Ultrastructure in Candida albicans", Can. J. Microbiol. Vol. 30 (1984) pp. 857–863; Miyata, M.; T. Kanbe & K. Tanaka: "Morphological Alterations of the Fission Yeast *Schizosaccharomyces pombe* in the Presence of Aculeacin A: Spherical Wall Formation, J. Gen. Microbiol. Vol. 131 (1985) pp. 611–621; Perez, P.; Garcia-Ascha & A. Duran: "Effect of Papulacandin B on the Cell Wall and Growth of Geotrichum Lactis, J. Gen. Microbiol. Vol. 129 (1983) pp. 245–250; Perez, P.; R. Varona, I Garcia-Acha & A. Duran: "Effect of Papulacandin F and Aculeacin A on $(1,3)$-$\beta$ glucan synthase from *Geotrichum lactis*", FEBS. Lett. 129, pp.249–252, 1981; Kopecka, M.: "Lysis of Growing Cells of *Saccharomyces cerevisiae* Induced by Papulacandin B", Folia Microbiol. Vol. 29 (1984) pp. 115–119; Taft, C.; T. Stark & C. Selitrennikoff: "Cilofungin (LY121019) Inhibits *Candida albicans* $(1,3)$-$\beta$-glucan Synthase Activity, Antimicrobial Agents Cheomother", Vol. 32, pp.1901–1903, 1988; and Phelps, P; T. Stark & C. Selitrennikoff: "Cell-wall Assembly of *Neurospora crassa*: Isolation and Analysis of Cell-Wall-Less Mutants", Current Microbiol Vol. 2 (1990) pp. 233–242. In each case, when the functioning of $(1,3)\beta$-glucan synthase was reduced either by drug treatment or by mutations that alter the level of substrate or enzyme activity, resulting cell-wall assembly and morphogenesis were abnormal, that is, cell walls either grew poorly or lysed.

It is known that $(1,3)\beta$-D-glucan synthase (E.C.2.4.1.34 UDP-glucose: 1,3-$\beta$-D-glucan 3-$\beta$-glucosyl transferase) catalyzes the polymerization of glucose ([1–3]-$\beta$-linkages) using UDP-glucose as substrate (the $K_m$ values range between 0.1 mM to 5 mM depending on source of the enzyme), although it has been reported in one instance that GDP-glucose was the preferred substrate. There is little known, however, concerning the structural requirements and order of binding for catalysts. By analogy with other glucosyl transferases, it is likely that the polymerization reaction involves the substrate acting as an electrophile while the glucan chain participates as a nucleophile. Enzyme activity is particulate and localized to the plasma membrane, while the in vitro pH optimum is typically between pH 7 and pH 8. Enzyme activity does not require a divalent metal ion, does not use a lipid-linked intermediate, and activity is not zymogenic, i.e. not proteolytically activated, and enzyme activity does not require a primer. A GTP-binding protein seems to play an important regulatory role and can be dissociated from "core" enzyme activity. Further, $\beta$-linked disaccharides are activators; inhibitors include uridine nucleotides, Neopeptins, Aculeacin A, Echinocandin B, gluconolactone, Papulacandin B, sorbose and Cilofungin. The site for substrate hydrolysis is cytoplasmic facing and the resulting glucan polymer is vectorially synthesized to the extracytoplasmic face of the plasma membrane. $(1,3)\beta$-glucan synthase is found in essentially all groups of fungi and is also present in plants (callose synthase).

Although detailed comparisons between fungal and plant glucan synthase have not been done, recent results show that enzyme activity from fungi and plants is multimeric. However, differences between $(1,3)\beta$-glucan synthase of fungi and plants are emerging. For example, plant $(1,3)\beta$-glucan synthase activity requires $Ca^{2+}$ and $Mg^{2+}$ but is not activated by GTP; fungal $(1,3)\beta$-glucan synthase requires neither ion and is activated by GTP.

One approach to the study of cell-wall assembly has been the genetic dissection of polymer synthesis. This has involved several strategies, one of which has been to characterize mutants and genes conferring resistance to killer toxins that bind $\beta$-glucans or inhibit $\beta$-glucan synthesis. This strategy has led to the hypothesis of a complex pathway of synthesis and incorporation of $(1,6)\beta$-glucan into the cell wall in *Saccharomyces cerevisiae*, as described by Brown et al. in Genetics, Vol. 133, (1993) pp.837–849. In addition, mutation of one killer-toxin-resistance gene affects both $(1,6)\beta$-glucan and $(1,3)\beta$-glucan syntheses. Two genes affecting $(1,3)\beta$-glucan synthesis were isolated using a killer toxin that inhibits $(1,3)\beta$-glucan synthesis.

Another strategy used in the prior art to isolate genes involved in $\beta$-glucan synthesis has been to screen for mutants with altered morphology that require osmotic support for growth. Two *Aspergillus nidulans* mutants with reduced amounts of cell wall (1,3)β-glucan were isolated according to the procedure of Borgia, P. T. & Dodge, C. L. described in *J. Bacteriol*, Vol. 174 (1992) 377–383. Two groups of osmotic remedial mutants of *Schizosaccharomyces pombe* having reduced levels of (1,3)β-glucan synthase activity were identified. One of these (1,3)β-glucan synthase mutants was shown to have a defective β subunit of geranylgeranyltransferase type I. See Diaz, M.; Sanchez, Y.; Bennett, T.; Sun, C. R.; Godoy,C.; Tamanoi,F., Duran, A.& Perez, P. (1993), *EMBO J*. 12, 5245–5254. Although there has been some success in the isolation and characterization of genes involved in cell wall β-glucan synthesis, analysis of these genes, especially those implicated in (1,3)β-linked glucan synthesis, has not resulted in a unifying model of polymer synthesis and cell-wall formation.

It can be seen from the foregoing that a detailed characterization of the (1,3)β-glucan synthase complex is needed, along with the characterization of a (1,3)β-glucan synthase genes and various antisense constructs against the gene. This basic information and understanding of (1,3)β-glucan synthesis and its regulation, subsequent cell-wall assembly and resulting growth and development of fungi is essential to the design and discovery of novel antifungal antibiotics.

SUMMARY OF THE INVENTION

The present invention is a cell-wall-less (1,3)β-glucan synthase gene and antisense constructs against the gene useful in the research and development of anti-fungal drugs. As has previously been described, a key step in fungal wall assembly, hyphal growth and development is the synthesis of (1,3)β-linked glucan. Because β-glucan is not made by humans, (1,3)β-glucan synthase is an attractive target for development of new antifungal antibiotics. It is the object of the present invention to characterize and reproduce a (1,3) β-glucan synthase gene by functional complementation of a cell-wall-less (1,3)β-glucan synthase mutant, and to design various antisense constructs against the gene. Then, subcloning the gene in the antisense direction and contacting within a quinic acid inducer is shown to inhibit fungal cell wall growth.

In accordance with the process described herein, a (1,3) β-glucan synthase gene has been cloned and the cDNA sequence and polypeptide amino acid sequence of the gene has been established. The gene of the present invention is embodied in an activating sequence of CDNA having a sequence SEQ. ID No: 1 derived from *Neurospora crassa* osmotic (1,3)β-glucan synthase gene, and further includes the polypeptide derived therefrom having the amino acid sequence Seq. ID No. 2.

Various antisense constructs were designed against the gene, gs-1, and *Neurospora crassa* was transformed with these constructs. The antisense gs-1 was under the inducible regulation of an exogenous promoter, (qa-2) to allow for the controllable regulation of the antisense message.

In contrast to the methods of the prior art, the approach to the study of (1,3)β-glucan synthesis disclosed herein has involved the purification of (1,3)β-glucan synthase activity and the isolation and characterization of (1,3)β-glucan synthase mutants of Neurospora crassa. Cell-wall-less mutants were isolated by mutagenesis of a temperature-sensitive protoplast-forming osmotic-1 mutant of *Neurospora crassa* and then screening for strains that did not regenerate cell wall. Twenty-four mutants that did not regenerate cell wall were isolated, twenty-two of which were found to have significantly reduced levels of (1,3)β-glucan synthase activity, while none had reduced levels of chitin synthases.

Next, the (1,3)β-glucan synthase mutants were classified into three complementation groups. Disclosed herein is the cloning and characterization of the glucan synthase 1 gene, gs-1, which complemented one group (group III) of the cell-wall-less (1,3)β-glucan synthase defective mutants.

Initially, (1,3)β-glucan synthase mutants were generated according to the procedure of Phelps et al., 1990, in a temperature-sensitive osmotic mutant of *Neurospora crassa*, os-1, (NM233t)A nicl (S1413)a, then grown as a population of protoplasts at the non-permissive temperature of 37° C. as described in C. P. Selitrennikoff et al., "Formation and Regeneration of Protoplasts Derived from a Temperature Sensitive Osmotic Strain of *Neurospora Crassa*," Exp. Mycol. Vol. 5 (1981) pp. 155–161.

It is known that when transferred to the permissive temperature of 25° C. these protoplasts regenerate cell walls and hyphae. The osmotic mutant has (1,3)β-glucan synthase activity at both the permissive and non-permissive temperatures. The protoplasts of the osmotic mutant were then grown at the non-permissive temperature, mutagenized with EMS, and plated out at the permissive temperature. Colonies that did not regenerate cell walls (cw$^-$) were characterized.

Of the colonies that did not regenerate cell walls, twenty-four cw$^-$ mutants were obtained. All twenty-four had normal levels of chitin synthase activity. Twenty-two of the mutants were observed to have very low levels of (1,3)β-glucan synthase activity (gs$^-$) while two showed normal levels.

Complementation between the mutants could not be done either by mating because the mutations are ascospore lethal or by forced heterokaryosis because all the mutations were generated in the same parent strain and therefore have the same auxotrophic marker. As such, of the 22 gs$^-$ mutants, one was selected based on its ability to complement the gs$^-$ and cw$^-$ defects of slime mutants, and is referred to herein as the strain TM1.

In accordance with the present invention, a (1,3)β-glucan synthase gene was then cloned. To this end, pools of cDNA were prepared from the *Neurospora crassa*, pMOcosX genomic library obtained from the Fungal Genetics Stock Center. The purified cDNA was transformed into the (1,3) β-glucan synthase mutants, TM1, by selecting for the hygromycin-resistant gene on the cosmid. Fifteen thousand seven hundred hygromycin-resistant transformants of the cw$^-$ gs$^-$ mutants were screened by plating 30–125 transformants per plate and examining individual colonies for hyphal growth. Four hyphal transformants were found among the TM1 transformants.

The wild-type DNA that transformed the TM1 strain was from two cosmid pools. Sub-pools of one positive pool were prepared. Hyphal transformants were observed at a frequency of 1/100 and 1/1000 from two of those sub-pools. The sub-pool with the higher frequency of complementation was then subdivided until two single cosmids were demonstrated to complement the TM1 cw$^-$ defect. The complementing cosmids were from wells G23:3H and G23:5G of the pMOcosX ordered library. Digestion with restriction enzymes indicated that the cosmids appear to be overlapping clones.

To subclone the DNA fragment required for complementation of TM1, G23:5G DNA was digested with restriction enzymes singly and in combination, and transformed directly into TM1. The cDNA digested with PstI and HindlII complemented the cw$^-$ defect of TM1. A 4.7kb PstI/HindIII fragment complemented the cw$^-$ defect of TM1 and was cloned into pBluescriptSK(-). A restriction map of the 4.7 kb fragment is shown and described subsequently.

A 1.8 kb PstI/EcoRI fragment subcloned from the 4.7 kb fragment also complemented the TM1 cw⁻ defect. Next, transformation of TM1 with cosmid G23:3H or the 4.7 kb cloned fragment restored (1,3)β-glucan synthase activity.

The 1.8 kb gs-1 fragment was used to isolate cDNA clones by hybridization from a *Neurospora crassa* mycelial λZap library obtained from the Oregon Graduate Institute (Dr. M. Sachs). One cDNA clone, pAF7, contained a 2.7 kb insert that hybridized to the 1.8 kb gs-1 fragment which suggested that the 1.8 kb gs-1 fragment may not contain the entire gene.

Next, utilizing the Northern Blot technique, blots of total RNA, isolated at various times of growth of germinating macroconidia, were probed with the 1.8 kb gs-1 fragment labeled with [$\alpha$-$^{32}$P]dCTP. A single band of RNA migrating at approximately 3 kb was detected. The gs-1 transcript appeared at the highest level at 0.5 hours of germination, suggesting that gs-1 expression is developmentally regulated.

To show inhibition of *N. crassa* (1,3)β-glucan synthase function, several antisense constructs were made against glucan synthase-1 (gs-1). The various antisense constructs were transformed into wild type *Neurospora crassa* and growth inhibition was observed under induction. One of the antisense transformants, pMYX107, exhibited inducible inhibition of growth on agar plates and in race tubes. Light microscopy revealed an abnormal hyphal morphology. The induced pMYX107 transformant also had only 40% the (1,3)β-glucan synthase activity of non-induced cultures.

DETAILED DESCRIPTION OF THE INVENTION

Figure 1:
FIG. 1 is a restriction map of a DNA fragment characterizing a gene which complements a cell wall-less (1,3)β-glucan synthase mutant.

The gene of the present invention is embodied in an activating sequence of cDNA having a sequence SEQ. ID No: 1, derived from the *Neurospora crassa* (1,3)β-glucan synthase-1 gene. The gene of the present invention further includes the polypeptide derived therefrom, having amino acid sequence SEQ. ID No: 2.

Various antisense constructs were made against the gene isolated and cloned herein. The gene was then subcloned in the antisense direction into a *Neurospora crassa* expressing vector downstream from the inducible qa-2 promoter. Each antisense construct was transformed into wild type *Neurospora crassa* and contacted with quinic acid inducer. The results showed inhibited cell wall growth. The gene and processes described herein are effective in different ways in developing new antifungal antibiotics.

The terms and expressions which have been employed are used as terms of description and not of limitation, and there is no intention in the use of such terms and expressions of excluding any equivalents of the features shown and described or portions thereof, it being recognized that various modifications are possible within the scope of the invention. Other applications of the invention described herein will be apparent to the skilled artisan and need not be repeated here.

In accordance with the method of the present invention is the isolation of a (1,3)β-glucan synthase gene by the functional complementation of a cell-wall-less (1,3)β-glucan synthase mutant. The results disclosed and described indicate that the gs-1 gene product is required for (1,3)β-glucan synthase activity and cell-wall formation of *Neurospora crassa*. In addition, the results indicate that there is only one (1,3)β-glucan synthase enzyme in *Neurospora crassa* or that the gs-1 gene product disclosed is required for each (1,3)β-glucan synthase activity measured under the in vitro conditions used.

A specific example of the steps employed in isolation of a (1,3)β-glucan synthase gene and then cloning the gene are herein provided. A second example describes the formation of antisense constructs and the inducible inhibition of fungal cell wall growth. These examples are to illustrate and demonstrate the method of the invention, and are not intended to limit the scope, utility, or applicability of this invention.

EXAMPLE 1

MATERIAL AND METHODS

STRAINS AND CONDITIONS OF CULTURE

The *Neurospora crassa* os-1 (NM233t) A and nic-1 (S1413)a were obtained from the Fungal Genetics Stock Center (in Kansas City, Kans.) and crossed to obtain os-i nic-1 a progeny. As described by Selitrennikoff et al. in Exp. Mycol. Vol 5 (1981) pp. 155–161, cultures of the osmotic 1 mutant (os-1 nic-1 a) were grown at 37° C. as a population of protoplasts; when cultures were shifted to 25° C., protoplasts regenerated hyphae. A (1,3)β-glucan synthase cell-wall-less mutant, TM1, was derived from the osmotic-1 mutant by ethylmethanesulfonate mutagenesis as described in Phelps et al. in Current Microbiology Vol. 21 (1990) pp. 233–242.

GROWTH AND HARVESTING

Protoplasts were grown in Vogel's medium N supplemented with 7.5% (wt/vol) sorbitol and 1.5% (wt/vol) sucrose (SS medium). Liquid cultures were incubated at 37° C. with shaking at 140 rpm. For solid medium, 1.25% (wt/vol) agar was added. Strains requiring nicotinamide were grown in medium supplemented with nicotinamide at 10 μg/ml.

*Escherichia coli* media LB, 2x YT, and NZYM, and *Escherichia coli* strains LE392, XL1-Blue, DH5, and DH5α are described by Sambrook et al. in "Molecular Cloning: A Laboratory Manual" Cold Spring Harbor Lab. Press, 2nd Ed. (1989).

PREPARATION OF cDNA

The Orbach/Sachs cosmid library (pMOcosX; Orbach, M. J. and Sachs, M. S., Fungal Gen. Newslett., Vol. 38 (1991)p. 97 was obtained from the Fungal Genetics Stock Center as 50 96-well microtiter plates (G1-G25 and X1-X25). Each well contains one *Escherichia coli* DH5αMCR transformant frozen in LB medium supplemented with 10% (vol/vol) glycerol and ampicillin (50 μg/ml). Microtiter plates were thawed and wells were replicated onto LB solid medium containing ampicillin (50 μg/ml). After incubation of the replicated plates at 37° C. overnight, cells were scraped off and suspended in 40 ml of LB medium containing ampicillin (50 μg/ml). These cultures were incubated at 37° C. at 225 rpm for 2 hours, then cells were harvested. cDNA was isolated using a gentle alkaline lysis protocol, lithium chloride precipitation, and centrifugation in CsCl-ethidium bromide gradients.

SIB SELECTION

Individual cosmids that complemented the cell-wall-less defect of TM1 were isolated using the sib selection procedure of Akins and Lambowitz, Molecular Cell. Biol. Vol.5 (1985) pp. 2272–2278. TM1 was transformed (see below) with 480-clone pools, 48-clone pools, 8-clone pools, and then DNA from individual wells of the Orbach/Sachs cosmid library.

TRANSFORMATION

The protoplasts were transformed using a modification of the Vollmer-Yanofsky procedure, Proc. Natl. Acad. Sci. USA, Vol. 83 (1986) pp. 4869–4873. Aliquots of the transformation mixtures were spread onto plates containing a 7-ml agar-solidified SS medium layer over a 25-ml bottom layer of agar-solidified SS medium supplemented with hygromycin (Calbiochem) at 150 units/ml or benomyl (DuPont) at 250 ng/ml.

ASSAY OF (1,3)β-GLUCAN SYNTHASE ACTIVITY

Protoplasts were grown to a density of $1-6\times10^6$ cells per ml and harvested by centrifugation (500×g, 5 min, 4° C.). Cell pellets were washed with ice-cold 7.5% sorbitol/1.5% sucrose/25 mM Hepes, pH 7.4, and lysed by suspension in 25 mM Hepes, pH 7.4/10 mM $NaH_2PO_4$/600 mM glycerol/5 mM EDTA/10 mM NaF/10 μM guanosine 5'-[y-thio] triphosphate/1 mM dithiothreitol. (1,3)β-glucan synthase activity of cell lysates was assayed with slight modifications of the procedure as described in D. R. Quigley and C. P. Selitrennikoff Exp. Mycol. Vol. 13 (1984) pp. 202–214. The cell lysate (20 μl containing 25–300 μg of protein) was combined with a 6-μl reaction mixture containing 50 μg of α-amylase and ≈50,000 cpm of UDP[U-$^{14}$C] glucose (ICN). The final concentration of UDP glucose was 1.15 mM. Protein content of cell lysates was determined by the Bradford method, Anal. Biochem. Vol. 72 (1976) pp. 248–254, using the Bio-Rad protein dye reagent.

PRODUCT CHARACTERIZATION

The radioactive reaction product formed in selected (1,3) β-glucan synthase assay mixtures was incubated with bovine serum albumin (control), α-amylase, or exo-1,3-β-D-glucanase as described by M. Hrmova, C. S. Taft & C. P. Selitrennikoff in Exp. Mycol. Vol. 13 (1989) pp. 129–139, to confirm that the product was (1,3)β-linked glucan.

ISOLATION OF gs-1 cDNA CLONES

The gs-1 CDNA clones were isolated from a Neurospora crassa λZAP I cDNA library (from the Oregon Graduate Institute). The library was screened with a 1.8-kb genomic gs-1 fragment, labeled with [$^{32}$P]dCTP (Amersham) by random prime labeling using the Benton-Davis in situ plaque hybridization procedure as modified by Sambrook et al., "Molecular Cloning, A Laboratory Manual", Cold Spring Harbor Press, Plainview, N.Y. 2nd Ed. (1989). pBluescript SK(-) derivatives containing gs-I cDNAs were obtained from gs-1 containing λZAP I clones by in vivo excision using the helper phage R408. See J. M. Short, J. M. Fernandez J. A. Sorge & W. D. Huse, (1988) Nucleic Acids Res. Vol. 16 pp. 7583–7600.

DNA SEQUENCING

DNA sequencing was done by the dideoxynucleotide method described by F. Sanger et al. in Proc. Natl. Acad. Sci., USA, Vol. 74 (1977) pp. 5463–5467, using Sequenase Version 2.0 (United States Biochemical), adenosine 5'-[α-[$^{35}$S]thio] triphosphate (Amersham), gradient polyacrylamide gels, and T3 and T7 primers. Sequencing templates were made by preparing nested sets of exonuclease III deletions and isolating single-stranded DNA from the pBluescript SK(-) derivatives in Escherichia coli XL1-Blue using the helper phage VCSMI3.

RESTRICTION FRAGMENT LENGTH POLYMORPHISM MAPPING of gs-1.

The gs-1 containing cosmid G23:3H digested with EcoRI was labeled with digoxigenin-dUTP by random priming using Genius kit, from Boehringer Mannheim, and used to probe a Southern blot of DNA from the small set of restriction fragment length polymorphism progeny digested with Sph I. Unlabeled pMOcosX was added to the hybridization mixture as unlabeled competitor for the labeled vector sequences.

ISOLATION AND SOUTHERN BLOT ANALYSIS OF GENOMIC DNA

Genomic DNA was isolated as described by Yarden and Yanofski in Genes Development, Vol. 5 (1991) pp. 2420–2430, with the following modification: after ethanol precipitation, DNA was suspended in 10 mM Tris-HCl/1 mM EDTA, pH 8.0, incubated 1–2 hours at 37° C. with RNase A (50 μg/ml), precipitated with isopropanol, rinsed in 70% (vol/vol) ethanol, dried, and resuspended in 10 mM Tris.HCl/I mM EDTA, pH 8.0.

DNA digested with restriction enzymes and separated on agarose gels was transferred to Zeta-Probe GT membrane (Bio-Rad) or Hybond-N membrane (Amersham) and hybridized at high stringency with $^{32}$P-labeled DNA according to the membrane manufacturers' recommendation.

DISRUPTION OF gs-1

The chromosomal copy of the gs-1 gene was deleted using a one-step gene replacement method described by Cullen et al. Gene, Vol. 57 (1987) pp.21–26. A selectable marker, the benomyl-resistant allele of β-tubulin (Bml, called tub-2) was flanked with a 1.5-kb EcoRI-HindIII upstream genomic fragment and a 1.9-kb HindIII-SalI downstream genomic fragment. This gene replacement construct was digested with NotI and SalI and transformed into protoplasts of the osmotic-1 mutant. Genomic DNA isolated from benomyl-resistant transformants was individually digested with EcoRI, HindIII, and SalI, electrophoresed on agarose gels, and screened for the absence of gs-1 containing DNA and the presence of the Bml DNA by Southern blot analysis.

RESULTS

CLONING OF THE GLUCAN SYNTHASE 1 GENE

The (1,3)β-glucan synthase-deficient mutant of Neurospora Crassa, TM1, was isolated previously by mutagenizing cells of the protoplast-forming osmotic-1 mutant and screening for cultures that did not regenerate cell wall. TM1 was transformed with pools of DNA from the Orbach/Sachs genomic library and plated onto a medium containing hygromycin. Of 17,700 hygromycin resistant transformants visually examined for hyphal regeneration, four hyphal transformants were obtained. Hyphal transformants were only observed when TM1 was transformed with DNA pools from library plates G11-G15 and G21-G25. As described in connection with example 4, single cosmids that complemented TM1 were isolated from the G21-G25 plates by the sib selection procedure. cDNA from wells G23:3H and G23:5G individually complemented the cell-wall-less defect of TM1.

To subclone the gs-1 gene, G23:5G DNA was digested with restriction endonucleases singly and in combination. The digested CDNA was cotransformed into TM1 with a plasmid containing the benomyl-resistant allele of β-tubulin and resulting benomyl-resistant transformants were screened for hyphal growth. cDNA digested with PstI and HindIII complemented the cell-wall-less defect of TM1 and a 4.7-kb Pst I fragment from G23:5G that complemented the cell-wall-less defect of TM1 was subcloned. Approximately 2.9 kb of the complementing 4.7-kb fragment contained only cosmid vector sequences. The remaining 1.8-kb contained primarily genomic *Neurospora crassa* DNA and complemented the cell-wall-less defect of TM1.

gs-1 DNA COMPLEMENTED THE (1,3)β-GLUCAN SYNTHASE ACTIVITY DEFECT OF TM1

TM1 cells transformed with a control plasmid containing a hygromycin-resistance gene, the 1.8-kb gs-1 fragment or the gs-1-containing cosmid G23:3H were grown and harvested, and cell lysates were assayed for (1,3)β-glucan synthase activity. As shown in Table 1, the (1,3)β-glucan synthase activity of TM1 transformed with the control plasmid was only 6% of the activity of the parental strain, the osmotic-1 mutant. In contrast, cells transformed with either the gs-1-containing cosmid G23:3H or a plasmid containing the 1.8-genomic gs-1 fragment had 41% and 29% respectively, of the level of the (1,3)β-glucan synthase activity of the parental osmotic-1 mutant, as shown in Table 1. Approximately 85% of the radioactive product formed by extracts of TM1 cells transformed with the 1.8-kb gs-1 fragment were hydrolyzed by (1,3)β-glucanase but was not hydrolyzed by α-amylase, indicating that the product formed was (1,3)β-linked glucan.

TABLE 1

(1,3)β-Glucan synthase activities of TM1 and the osmotic 1 mutant transformed with gs-1-containing plasmids or a control plasmid

| | | (1,3)β-Glucan synthase activity | |
|---|---|---|---|
| Strain | Plasmid | Specific activity | % of os-1 nic-1 a |
| os-1 nic-1 a | pMP6 | 2.0 ± 0.75 | 100 |
| TM1 | pMP6 | 0.12 ± 0.11 | 6 |
| TM1 | pCE105 | 0.58 ± 0.37* | 29 |
| TM1 | G23:3H | 0.84 ± 0.53* | 41 |

*Note: Activities are significantly different (P < 0.001) from the activity of TM1 transformed with no qs-1 DNA (pMP6).

As seen in Table 1, TM1 and the osmotic mutant (os-1 nic-1 a) were transformed with the indicated plasmids. Liquid cultures of hygromycin-resistant transformants were grown as protoplasts at 37° C. and harvested, and lysates were assayed for (1,3)β-glucan synthase activity. Specific activity is nmol of glucose incorporated into (1,3)β-linked glucan per min per mg of protein. Data are mean ± SD, based on 7–20 data points from 2–10 transformants for each value. The plasmid pMP6 contains a hygromycin-resistance gene, but does not contain gs-1 DNA. The plasmid pCE105 contains a hygromycin-resistance gene and a 1.8-kb genomic gs-1 fragment. The cosmid G23:3H contains a hygromycin-resistance gene and a gs-1 containing genomic DNA fragment.

SEQUENCE OF gs-1

The 1.8-kb gs-1 fragment was labeled with [$^{32}$P]dCTP and used to probe a Northern Blot of RNA isolated from germinating Neurospora crassa macroconidia. Only a single transcript of ≈3 kb was detected. The labeled 1.8-kb gs-1 fragment was also used to screen a mycelial cDNA library and a 2585-nucleotide gs-1 cDNA was isolated and sequenced.

The coding sequence of the gs-1 gene appeared to the contained within a 3.25 kb PstI/SmaI fragment shown in the highlighted box of the restriction map of shown in FIG. 1. In this map, the following abbreviations are used:

B=BamHI

Bg=BglII

E=EcoRI

H=HindIII p=PstI

S=SalI

Sm=SmaI

X=XhoI

The marked 3.25 kb fragment complemented the TM1 cell-wall-less defect. Transformation of the TM1 mutant with cosmid G23:3H restored (1,3)β-glucan synthase activity.

The gs-1 cDNA sequence is appended hereto as SEQ. ID. No: 1 (SEQ. ID No. 1). The amino acid sequence of the polypeptide encoded by DNA corresponding to SEQ. ID No: 1 is appended hereto as SEQ. ID. No: 2 (SEQ. ID No. 2). Referring to the attached cDNA sequence of 2585 nucleotides, the sequence predicts an open reading frame coding for a protein of 535 amino acids, molecular weight of 58.9 kDa. The translational initiation site (CAAAATGGCT), SEQ. ID. No: 3 , and codon usage (not shown) are similar to known Neurospora crassa genes. There are approximately 140 nucleotides and 850 nucleotides of 5' and 3' untranslated cDNA, respectively. Analysis of the predicted amino acid sequence revealed no eukaryotic signal sequences, suggesting that the protein is not secreted, and no transmembrane spanning domains, but a number of possible post-translation sites, such as sulfation site, protein kinase sites. There is one potential PEST region, and a number of clusters of amino acids, e.g. 5 P residues (124–128), 10 K residues (480–528). The protein is predicted to be a 38% α-helix.

THE 1.8-kb GENOMIC FRAGMENT

As described above, the 1.8-kb genomic gs-1 DNA fragment complemented the cell-wall-less (1,3)β-glucan synthase defect of TM1. However, restriction mapping and sequencing of the 1.8-kb gs-1 fragment revealed that it does not include the entire open reading frame coded by the 2585 cDNA. This truncated genomic fragment encodes a protein of ≈140 amino acids shorter (at the C terminus) than the native GS-1 protein and retains the region of high homology between Smil and GS-1 proteins, (results not shown). Complementation of the TM1 defect by the 1.8-kb gs-1 fragment could be due to either homologous recombination or to ectopic integration. However, the observation that the 1.8-kb DNA fragment contains 3' vector sequence and little 5' flanking sequence makes homologous recombination unlikely.

CHROMOSOMAL LOCALIZATION OF gs-1

Restriction fragment length polymorphism mapping was used to determine the chromosomal location of gs-1. Polymorphisms were observed when DNA from *Neurospora crassa* Oak Ridge and Mauriceville backgrounds was digested with a variety of enzymes and probed with the gs-1 containing cosmid G23:3H. When DNA from the small set of restriction fragment length polymorphism progeny was digested with Sph I and probed with G23:3H DNA, gs-1 segregated with the inl locus shown in Table 2, indicating that gs-1 is located on linkage group V.

TABLE 2

Segregation of restriction fragment length polymorphisms detected by G23:3H

| Marker | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| G23:3H | (O) | O | O | M | O | (M) | M | M | M | M | M | M | M | M | O | M | O | M | M | M |
| inl | (O) | O | O | M | O | (M) | M | M | M | M | M | M | M | M | O | M | O | M | M | M |

NOTES: Isolates 1–20 are Fungal Genetics Stock Center strains 4411–4430. Isolate 1 is RLM33-1a; isolate 6 is Mauriceville-1cA.O.RLM33-1a parental genotype; M, Mauriceville-1cA genotype. Parentheses surround the parental markers. The inl data are from Metzenberg et al.

DELETION OF gs-1

The chromosomal copy of the gs-1 gene of the osmotic mutant was replaced with the benomyl-resistant allele of β-tubulin, Bml, using DNA sequences that flank the gs-1 gene.

Cell lysates of a resulting gs-1 deletion strain, D7, had 3% of the (1,3)β-glucan synthase activity of osmotic-1 mutant cells transformed with a tub-2 containing plasmid (0.11±0.03 and 4.7±0.5 nmol per min per mg of protein, respectively; mean±SD; n=6). This value was similar to the activity of the original (1,3)β-glucan synthase-deficient strain, TM1. In addition, the small amount of $^{14}$C-labeled material produced by D7 in vitro(1,3)β-glucan synthase reaction mixtures was not digested by exo-(1,3)β-glucan synthase (results not shown), indicating that the gs-1 deletion strain contained no (1,3)β-glucan synthase activity.

EXAMPLE 2

MATERIAL AND METHODS

STRAINS AND MEDIA

*N. crassa* wild type (w.t.) strain (74-OR8-1a) was obtained from the Fungal Genetics Stock Center (Kansas City, Kans.). Stock cultures were grown in 250 ml flasks containing 50 ml solidified agar, Vogel's medium N(2) and 1.5% (w/v) sucrose for 2 days at 28° C., then transferred to 25° C. for an additional 3–5 day incubation. Stock flasks containing macroconidia were stored at −20° C. until used.

GROWTH AND HARVESTING

Inducible inhibition of growth was tested on the following medium: Vogel's salts, 0.2% xylose, with or without 0.4% quinic acid (pH 6.0). For solid medium 1.5% (w/v) agar was added. Liquid cultures were inoculated with 1×10$^5$ conidia/ml. Cultures were incubated at 28° C. with shaking in a Gyrotory® G-76 Water Bath Shaker (New Brunswick, Edison, N.J.) at 140 rpm for 36 hours.

*Escherichia coli* media Luria Broth (1% Bacto-tryptone, 0.5% Bacto-yeast extract, 1% sodium chloride), 5-bromo-4-chloro-3-indolyl β-D-galactopyranoside (X-gal), isopropylthio-β-galactoside (IPTG), competent cells (using strains XL1-Blue and DH5α), and transformation protocols are essentially as described by Sambrook et al. Briefly, 100 μl of *E. coli* competent cells were transformed with plasmid DNA (50–500 ng) and plated on LB agar supplemented with ampicillin (100 μg/ml). PBluescript (10 ng/ml) was used as a positive control for transformations. Plasmid DNA was isolated from putative transformants using either alkaline lysis or Wizard MiniPreps (Promega, Madison, Wis.). Cloned insert DNA was confirmed through restriction analysis as will be described below.

TRANSFORMATION

In order to make *N. crassa* protoplasts, macroconidial cultures were harvested in sterile ice cold water, filtered through sterile cheesecloth and inoculated into Vogel's medium N supplemented with 1.5% (w/v) sucrose. The conidia were grown with aeration (200 rpm) in a rotary shaker for either 9 hours at 16° C. or 6 hours at 30° C. Resulting cultures were harvested by centrifugation (7.5 min, 1400 rpm) and resuspended in 1M sorbitol, to which Novozyme (10 mg per 10$^9$ conidia) was added. The conidia were incubated at 30° C., 65 min with shaking 140 rpm. The protoplasts were harvested by centrifugation (10 min, 600 rpm) and washed one time with IM sorbitol, then once with sorbitol, Tris, CaCl$_2$. The final pellet was brought up in sorbitol, Tris, CaCl$_2$ and PEG, Tris, CaCl$_2$ and DMSO.

Protoplasts were transformed with plasmid DNA using a modification of the Vollmer-Yanofsky procedure. Transformants were selected on plates containing 7-ml agar-solidified SS medium (Vogel's medium N supplemented with 7.5% (w/v) sorbitol and 1.5% (w/v) sucrose) layered over 25-mls solidified SS medium supplemented with hygromycin (Calbiochem, La Jolla, Calif.) at 290 U/ml. Monokaryotic microconidia were isolated by growth on iodoacetate medium and transferred to slants containing Vogel's sucrose medium. Resulting homokaryotic macroconidia were used for the experiments described below and were maintained at −20° C. as described for wild type cells.

MOLECULAR BIOLOGY

Restriction endonucleases were purchased from New England BioLabs or GIBCO BRL and used in accordance with manufacturers protocol. Generally, 3–4 U of a restriction enzyme was used to digest up to one μg of plasmid DNA and incubated at the appropriate temperature for at least 4 hours.

Figure 2:
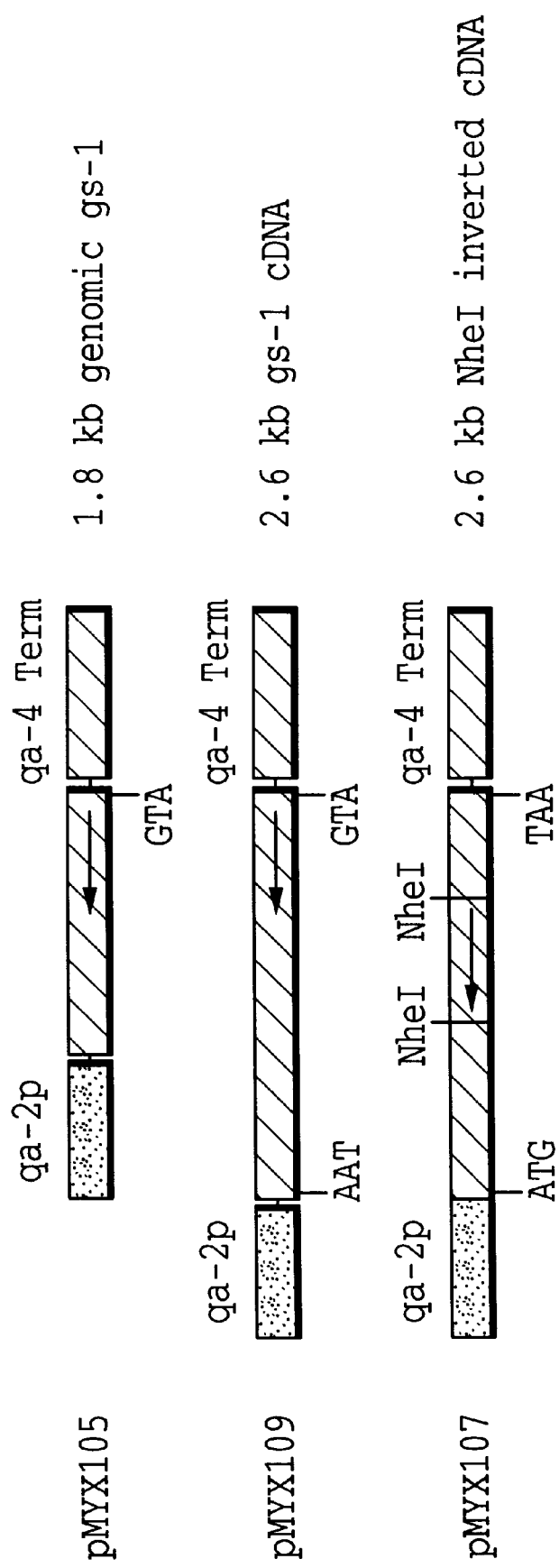
FIG. 2 is a map showing three gs-1 fragments cloned in the antisense direction into the unique Sma I site of the expression vector pMYX10.

Antisense fragments, as shown in FIG. 2, were subcloned into the unique SmaI site of the vector pMYX10 described by Campbell et al. The presence and orientation of the various antisense constructs were confirmed by restriction analysis.

Plasmid DNA from pMYX107 was used as the template for PCR amplification to confirm gs-1 antisense orientation within that construction. PCR primers were designed to hybridize to the vector sequence (qa-2P) at the 5' end and within the Nhel (antisense) sequence at the 3' primer. The primer sequences are as follows: forward primer GAA-GAGGGGGGGTCTCGCCCATTAATCC (SEQ. ID. No: 4) and reverse primer ATCCGACCAGGTTACGGAAAGC-CAAGCC (SEQ. ID. No: 5). Polymerase chain reaction (PCR) was used to confirm the antisense orientation of gs-1 within PMYX 107. PCR primers (5' GAA-GAGGGGGGGTCTCGCCCATTAATCC forward (SEQ. ID. No: 4) and 5' ATCCGACCAGGTTACGGAAAGC-CAAGCAGCC (SEQ. ID. No: 6) reverse) were designed to amplify a region from inside the qa-2 promoter sequence to within the Nhe 1 (antisense) sequence. The targeted DNA was amplified in a 50 μl reaction containing 1 μg of plasmid DNA, 0.5 μM primer, 200 μM dNTP's, 10 mM Tris-HCl (pH 8.3), 50 mM KCl, 1.5 mM MgCl$_2$, and 3.0 units of Taq DNA polymerase. Amplifications were performed on a Gene-Amp® 2400 thermal cycler (Perkin-Elmer, Norwalk, Conn.) with an initial cycle at 94° C. for 3 min, and subsequent 30 cycles at 94° C. for 30 sec, 60° C. for 30 sec, and 72° C. for 2 min.

PCR was also used to confirm the transformation of pMYX107 DNA within *N. crassa* wild type cells. Amplification conditions were changed slightly to include the addition of 10% DMSO to the 50 µl reaction, and the annealing temperature was optimized to 67° C. for 30 sec. The amplification products were visualized on a 1.0% (w/v) agarose gel in 1×TAE buffer and stained with ethidium bromide.

DNA EXTRACTION

Liquid cultures (30–50 ml) containing Vogel's medium N were inoculated with 1×10$^5$ conidia/ml. Cultures were incubated at 28° C. in a rotary shaker at 140 rpm for 36 hours. DNA was extracted according to a protocol by Taylor, et al. To this end, hyphae were harvested by vacuum filtration, and frozen overnight at −70° C. The hyphal pads were resuspended in an equal volume of lysis buffer (50 mM Tris-Cl, pH 8.0, 50 mM EDTA, 2% SDS, 1% β-mercaptoethanol) to which Rnase A was added (25 µg/ml final concentration) and incubated for 30 minutes at 37° C. Proteinase K was added (100 µg/ml final concentration) and incubated for 1 hour at 65° C. The samples were extracted with phenol then chloroform and washed with ethanol as described. The total yields were from 300–600 µg genomic DNA depending on the transformant.

RNA EXTRACTION

Liquid cultures (30–50 ml) containing 1X Vogel's salts, 0.2% xylose, with and without 0.4% quinic acid (pH6.0) were inoculated with 1×10$^5$ conidia/ml. Cultures were incubated at 28° C. in a rotary shaker at 140 rpm for 36 hours. RNA was extracted using RNA STAT-60 (Tel-Test "B", Inc; Friendswood, Tex.) reagent for total RNA isolation. Hyphae were harvested by centrifugation (10 min, 23,000×g, 0° C.) and resuspended in 10 ml of RNA STAT-60. Aliquots of the resuspension were put into 2-ml microfuge vials, half filled with sterile 0.5 mm zirconium-silica beads. The hyphae were disrupted (7×40 second pulses with 3 minute coolings between each pulse) using a mini-bead beater (Biospec Products, Bartlesville, Okla.). The rest of the protocol was followed according to manufacturers direction. In accordance with those directions, the samples were extracted 2 times with 1/5 volume chloroform, precipitated with 1/2 volume isopropanol, washed with 75% ethanol and harvested by centrifugation. The total yields ranged from 62 to over 100 µg RNA depending on the transformant.

PROTEIN EXTRACTION 500-ml flasks containing 250 ml media (0.2% xylose, 1× Vogel's salts with and without 0.4% quinate) were inoculated with 1×10$^5$ conidia/ml. Cultures were incubated at 28° C. for 36 hours at 140 rpm. Resulting hyphae were harvested by centrifugation (10 min. 19,600×g, 0° C.) and washed 2×'s with ice-cold water. The hyphae were harvested by centrifugation and used immediately.

To fresh hyphal pellets was added 20-mls of extraction buffer (25 mM HEPES (pH7.4); 10 mM NaH$_2$PO$_4$; 600 mM glycerol; 10 mM NaF; 5 mM EDTA and 10 µM GTPy-S). At 4° C., hyphae were disrupted (5×30 second pulses with 2 minute coolings between each pulse) using a Bead Beater (Biospec Products, Bartlesville, Okla.) with 0.5 mm zirconium-silica beads. Lysates were centrifuged at 1000×g for 10 min at 40° C., and used for the enzyme assays as will subsequently be described. Protein concentrations were determined by the method of Bradford using the Bio-Rad protein reagent (BioRad Labs, Hercules, Calif.). The yield was anywhere from 0.9–2.4 mg/ml crude extract depending on the transformant.

LIGHT MICROSCOPY

Liquid cultures (30–50 ml) containing 1× Vogel's salts (2), 0.2% xylose, with and without 0.4% quinic acid (pH6.0) were inoculated at 1×10$^5$ conidia/ml. Cultures were incubated at 28° C. with shaking in a rotary shaker at 140 rpm for 36 hours. Hyphae were viewed under a Zeiss-Axiophot microscope at 250× magnification and photographed.

ENZYME ASSAYS (1,3)β-Glucan synthase was assayed using modifications of a procedure previously described. To this end, in vitro reactions contained 50 µg α-amylase (type IIA; Sigma), 1 mM UDP-$^{14}$C-glucose (~50,000 cpm/assay), and 20 µl crude extract in a final volume of 26 µl. Reactions were carried out in V-bottom 96-well microtiter plates (Dynatec Laboratories, Chantilly, Va.) and incubated at 22° C. for 0, 15, 30, 45, and 60 minutes. Individual reactions were terminated by the addition of 50 µl 5% (w/v) TCA, followed by the addition of 200 µl water. The contents of each well were transferred to a Milliblot D apparatus (Millipore Corp.) containing an Inotech 201A glass fiber filter previously blocked with 5% (w/v) TCA containing 1% (w/v) sodium pyrophosphate. Each well was washed twice with 500 µl water, and dried under vacuum at 65° C. for 10 minutes before being wrapped in one layer of plastic wrap.

Wrapped Inotech glass fiber filters were placed for 4–18 hours on a Molecular Dynamics Phosphor Screen. The amount of radioactivity on the filter was determined using a Molecular Dynamics Phosphor Imager Model Sl. Pixel density/cpm (Phosphor Imager signal/cpm present) was converted to the number of pixels/nmol product ((1,3)β-glucan) formed.

Chitin synthase assays were performed essentially as described by Sburlati and Cabib.

RESULTS

FORMATION OF ANTISENSE CONSTRUCTS

The glucan synthase-1 gene (gs-1) has been previously isolated and is required for (1,3)β-glucan synthase activity as was shown and described in connection with Example 1. In order to observe the effects on *N. crassa* growth by decreasing (1,3)β-glucan synthase activity, various antisense constructs were made against the gs-1 gene. Two constructs, a 2.6 kb full length cDNA and a 3' truncated 1.8 kb genomic DNA have been previously obtained by functional complementation of a (1,3)β-glucan synthase deficient strain. In addition, a third construct was engineered so that only a 969 bp internal Nhel fragment of the 2.6 kb cDNA was inverted into the antisense direction, as seen with reference to FIG. 2. FIG. 2 shows three gs-1 fragments which were cloned in the antisense direction into the unique Sma I site of the expression vector pMYX10 described previously. The first of the fragments shown is the 1.8 kb genomic DNA including a 300 BP of 5' untranslated region (utr), 2 introns and the N-terminal end of the gs-1 coding region, but not the C-terminal end. The second fragment is a 2.6 kb cDNA fragment including the entire gs-1 coding region, 140 bp of 5' utr and 847 bp of 3' utr. The third fragment is the 2.6 kb cDNA in the sense direction with a 969 bp Nhe I fragment in the antisense direction. The pMYX10 vector allows for cloning of genes downstream of an inducible promoter (qa-2)p.

As described, each of these genes was subcloned in the antisense direction into a Neurospora expression vector pMYX10 downstream from the inducible qa-2 promoter. Therefore, the presence or absence of the inducer quinic acid in the media was used to regulate the gene expression of the antisense constructs.

INDUCIBLE INHIBITION OF GROWTH

Figure 3:
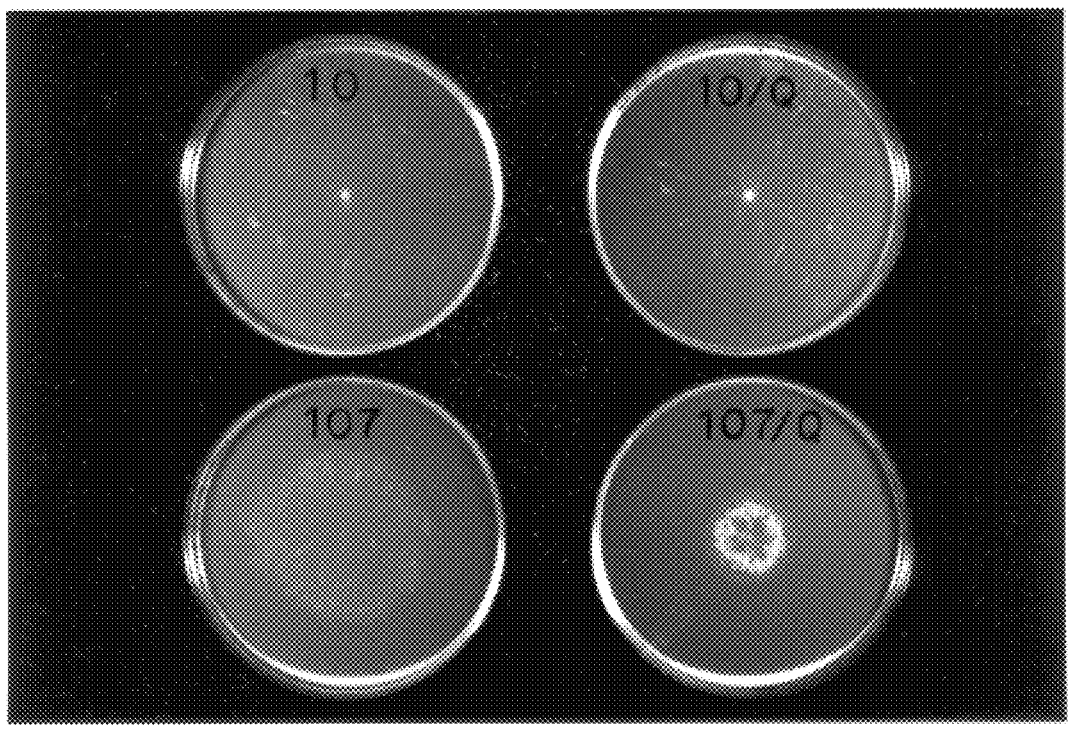
FIG. 3 is a micrograph illustrating the inducible inhibition of *N. crassa* growth using a gs-1 antisense construct as visualized on agar plates.

Each antisense construct was transformed into wild type *N. crassa* (74-OR8-1a) and selected for hygromycin resistance. In order to test if any of the constructs resulted in inducible inhibition of growth, the various transformants were screened on 0.2% xylose-agar plates either in the presence or absence of 0.4% quinic acid inducer. Of the 12 hyg$^r$ pMYX107 transformants screened, 6 exhibited growth inhibition in the presence of quinic acid (data not shown) and one of those four was chosen for further characterization, as illustrated with reference to FIG. 3. FIG. 3 is a photograph showing inducible inhibition of growth as visualized on agar plates. Hyphae were point inoculated in the absence or presence of quinic acid, as described above. The top two images in FIG. 3 show the pMYX10 transformant; the top left without quinic acid, the top right with quinic acid. The bottom two images show the pMYX107 transformant; the bottom left without quinic acid, the bottom right with quinic acid. All of the plates shown in FIG. 3 were photographed after 30 hours incubation at 25° C.

Transformants containing the other antisense or sense DNA constructs exhibited growth similar to wild type, that is the growth was not inhibited by quinic acid induction (data not shown).

To quantitate the slower growth of pMYX107, the transformants were grown in race tubes with xylose-containing medium with or without quinate. The growth rate of the induced pMYX107 transformant was only 30% that of the uninduced level, as determined by measuring the migration of the hyphal front, and 20% or 23% that of the induced pMYX10 transformant or wild type, respectively, as illustrated in Table 3 below.

TABLE 3

| Strain | Quinate | Growth Rate (cm/hr) | Standard Deviation (+/−) | % Growth after quinate induction |
|---|---|---|---|---|
| Wildtype[1] | − | 0.14 | 0.06 | |
| | + | 0.13 | 0.06 | 93% |
| pMYX10[2] | − | 0.16 | 0.05 | |
| | + | 0.14 | 0.06 | 87% |
| PMYX107[2] | − | 0.10 | 0.05 | |
| | + | 0.02 | 0.02 | 20% |

[1]n = 4; [2]n = 7

Table 3: Inducible Inhibition of growth as measured in race tubes. Growth rates (cm/hr) were calculated by measuring hyphal migration fronts (cm) at various time intervals (hours). Race tubes used the same media, strains and growth conditions as in FIG. 2.

ALTERED MORPHOLOGY SEEN IN GROWTH INHIBITED CELLS

Figure 4A:
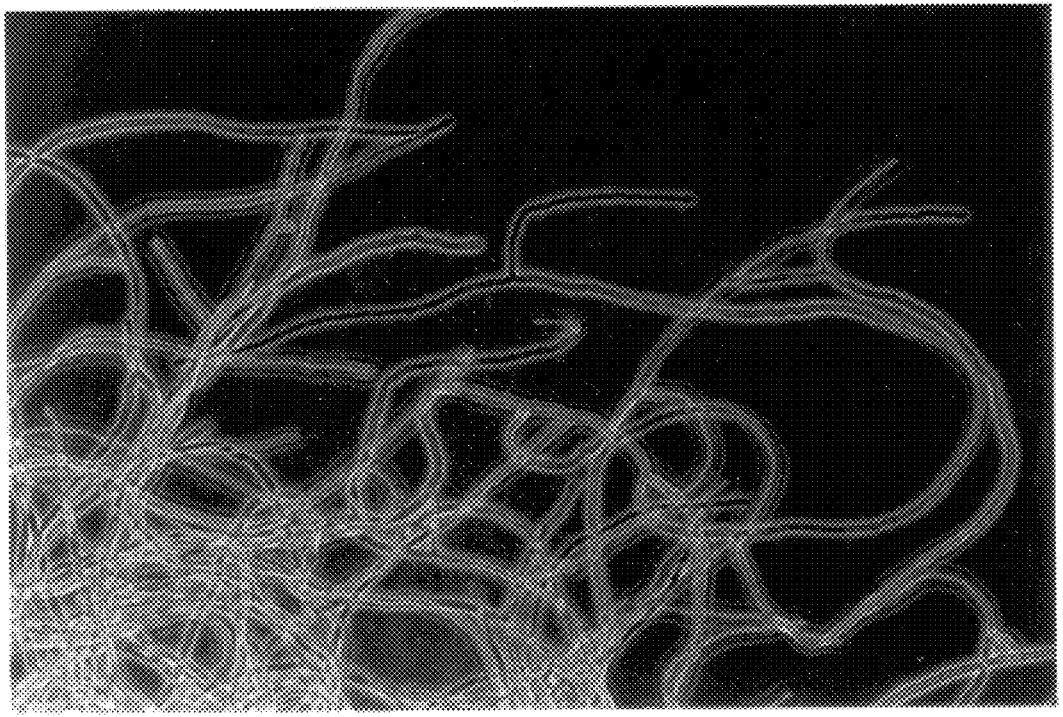
FIGS. 4A and 4B are light micrographs of the pMYX107 transformant.
Figure 4B:
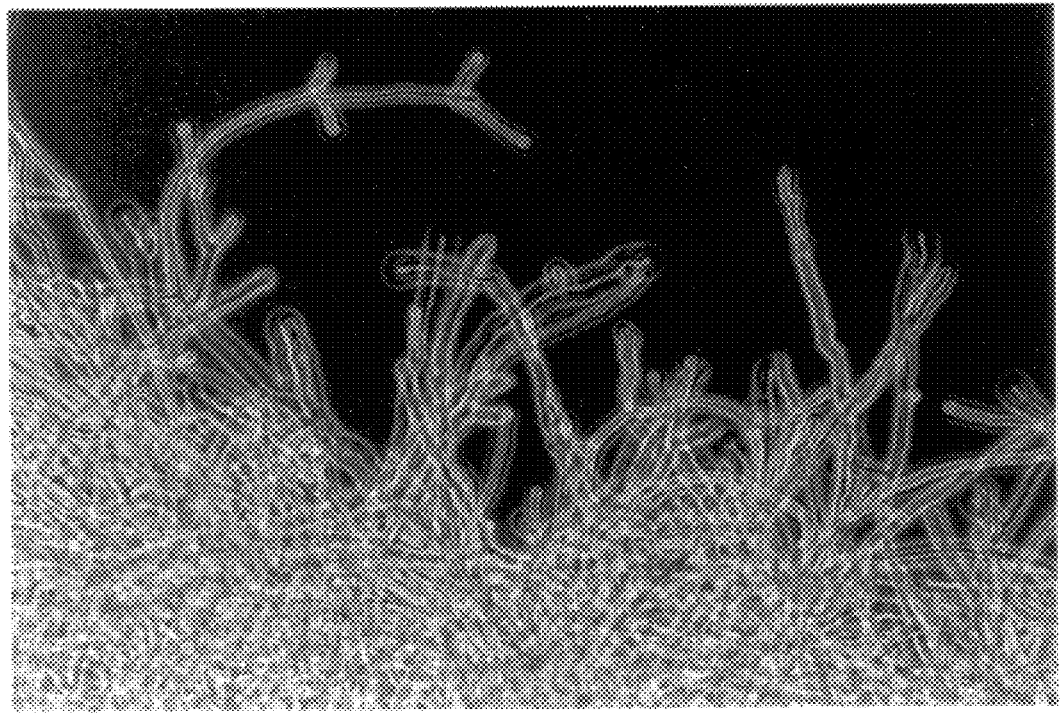

The pMYX107 transformant was further characterized to see if the hyphal morphology was any different after quinic acid induction. As shown in FIGS. 4A and 4B, which are light micrographs of the pMYX107 transformant, light microscopy of the pMYX107 transformant revealed that the hyphal length was significantly shorter in induced versus noninduced conditions. One possible explanation of this abnormal phenotype is that a decrease in the enzyme (1,3) β-glucan synthase resulted in shorter hyphae due to the decrease of (1,3)β-glucans available for incorporation into the cell wall.

With reference still to FIGS. 4A and 4B, the liquid cultures were inoculated with 1×10$^5$ condida/ml and incubated for 36 hours at 28° C. at 140 rpm before they were photographed. FIG. 4A show the uninduced conditions (without quinate) while FIG. 4B shows the induced conditions (with quinate).

(1,3)β-GLUCAN SYNTHASE ACTIVITY

Since the target of the pMYX107 antisense construct is the gs-1 gene, the growth inhibition observed after quinate induction should theoretically reflect a decrease of the target enzyme (1,3)β-glucan synthase. To test for this, (1,3)β-glucan synthase activity was measured from the pMYX107 transformant grown under both uninduced and quinic acid induced conditions. As controls for enzyme activity, wild type and the pMYX10 transformant were also assayed. The specific activity (nmol min$^{-1}$ mg$^{-1}$) of the 107 transformant was only 40% that of noninduced cells and 15% or 30% that of the induced pMYX10 transformant or wild type, respectively, as shown in FIG. 5.

Figure 5:
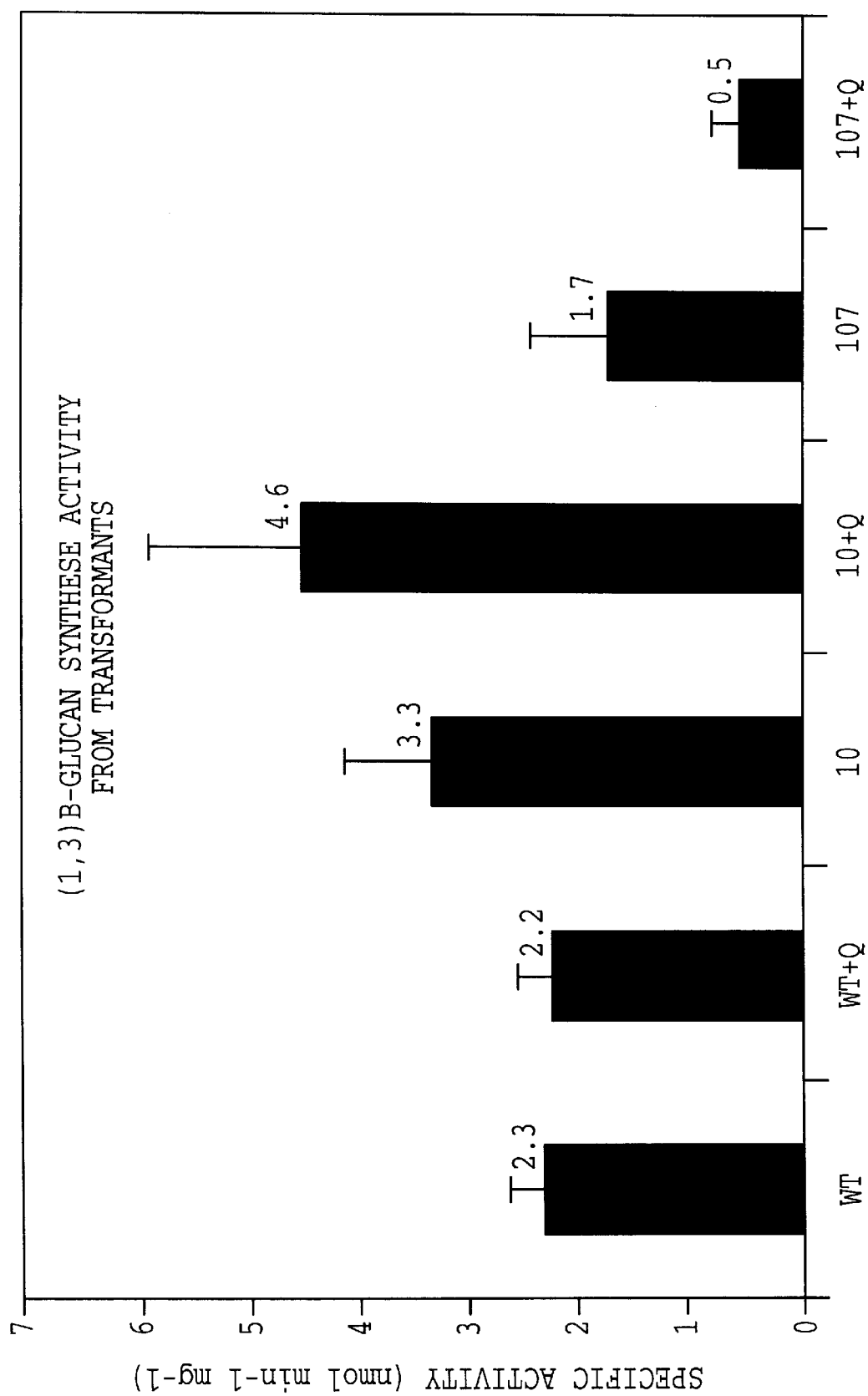
FIG. 5 is a bar chart showing the comparison of glucan synthase activities of wild type, the pMYX10 transformant and the pMYX107 transformant grown under non-induced v. induced conditions.

FIG. 5 is a bar chart showing the comparison of glucan synthase activities of the wild type, the pMYX10 transformant and the pMYX107 transformant grown under non-induced (without quinate) versus induced (with quinate) conditions. The liquid cultures were grown as described and shown in connection with FIG. 4. Hyphae were isolated, lysed and (1,3)β-glucan synthase activity assayed. In vitro reaction mixtures contained 1.2 mM UDP-[$^{14}$C]glucose (~50,000 cpm/assay) and 20 μl crude extract. Protein concentrations were measured using BioRad protein reagent from BioRad labs, Hercules Calif. Reaction mixtures were incubated at 25° C. for 0, 15, 30, 45, and 60 minutes. The reactions were terminated by the addition of 50 μl of 5% (w/v) TCA. The incorporation of radioactive glucose into (1,3)-β-D-glucan and velocities (nmol glucose per minute) were determined. Specific activity was calculated as nmol min$^{-1}$ mg$^{-1}$. Wt n=8; pMYX10 n=16; pMYX107 n≧14.

The buffer used for the glucan synthase assay had been optimized for wild type *N. crassa* grown in Vogel's medium N in which quinic acid was not present. The possibility that quinic acid in the growth medium might be trivially causing a decrease in the (1,3)β-glucan synthase assay was addressed. Concentrations as high as 4.0% of quinate added to the (1,3)β-glucan synthase did not show an inhibitory effect on wild type crude extract (data not shown). Since the concentration of quinate in the growth media was 0.4%, the presence of quinate alone was not inhibitory to the assay.

There was also some question as to whether the induction of antisense construct was globally affecting other cell wall enzymes, such as chitin synthase. To test for this possibility, the chitin synthase activity was measured using the same crude extracts described above for glucan synthase. The 107 transformant, however, exhibited chitin synthase activity comparable to both wild type strain and the pMYX10 transformant under uninduced and quinic acid induced conditions (data not shown). It seems, therefore, that the antisense construct showed specificity with regards to its target.

Described herein, in connection with Example 1, was the isolation of a (1,3)β-glucan synthase gene by the functional complementation of a cell-wall-less (1,3)β-glucan synthase mutant. The results disclosed and described subsequently indicate that the gs-1 gene product is required for (1,3)β-glucan synthase activity and cell-wall formation of *Neurospora crassa*. In addition, the results indicate that there is only one (1,3)β-glucan synthase enzyme in *Neurospora crassa* or that the gs-1 gene product disclosed is required for each (1,3)β-glucan synthase activity measured under the in vitro conditions used.

A small region of the gs-1 predicted amino acid sequence shown in SEQ. ID. No. 2, has significant sequence identity to the predicted protein of a *Saccharomyces cerevisiae* gene independently isolated by two groups. The region consists of only 83 amino acids, 16% of the predicted GS-1 protein. The yeast gene, called KNR4 or SMII, was independently isolated by two groups. The KNR4 gene was isolated by complementation of the cell wall defects associated with a knr4 mutation that conferred resistance to the killer toxin that inhibits (1,3)β-glucan synthesis.

The SMII gene was isolated by complementation of the growth defects associated with a smil mutation isolated in a screen for suppression of the inhibition of transcription by a matrix association region. The results of Fishel et al. show that the KNR4/SMII gene product is localized to the nucleus, suggesting that it is a transcriptional regulatory protein. The low overall sequence identity between GS-1 and Knr4/Smil proteins suggests that, although they may share a common functional domain (e.g., DNA binding), they are not direct homologs. Consistent with this idea is the observation that the gs-1 null mutant had essentially no (1,3)β-glucan synthase activity whereas the knr4 null mutant retained 33% of the activity of the wild type control.

It was speculated that the GS-1 protein is a transcriptional regulatory protein essential for the synthesis of genes coding for subunits of the (1,3)β-glucan synthase complex. This idea was supported by the 1.8-kb genomic DNA fragment, which retains the area of highest homology between GS-1 protein and the putative regulatory protein Smil and importantly, restores (1,3)β-glucan synthase activity and cell-wall formation to TM1.

As previously discussed, antisense RNA has successfully been shown by others to suppress viral infection in a bacterial or animal host. Disclosed herein, in connection with Example 2, was the use antisense methodologies in order to inhibit fungal growth. This suggests that antisense techniques can be used to study gene expression in fungal organisms and potentially lead to a new source of antifungal therapeutics.

It was observed that wild type *N. crassa* when transformed with pMYX107 (Nhe 1 internal antisense gs-1) is able to inhibit growth on agar plates and race tubes in a regulatable manner. The transformant containing gs-1 in the sense direction, however, was comparable to wild type (data not shown). It was also observed that a simultaneous decrease in the specific activity of the target enzyme in the pMYX107 transformant after induction. Even before induction the pMYX107 transformant exhibits lower specific activity of (1,3)β-glucan synthase than wild type levels suggesting that the qa-2 promoter is somewhat leaky and is transcribing message even in the absence of inducer.

Transformed DNA is able to integrate essentially anywhere along the chromosome so that each transformant is essentially unique. Therefore, the most stringent analyses can be made only within the same transformant. Since an inducible promoter was used, it was observed that phenotypes in the same transformant grown either in the presence or the absence of the inducer. Inhibition by the gs-1 antisense construction is not 100% as measured by growth rate and enzyme activity and reflects the potential to optimize the inhibitory sequence. Future experiments will include localizing the minimum antisense sequence required for inhibition. Also, not all of the antisense constructs tested successfully inhibited growth (i.e., the truncated genomic DNA and the full length cDNA). The reasons may give insight into the mechanism of inhibition. The pMYX107 construction may generate a more stable RNA species within the cells or maybe a unique secondary structure is formed that is suitable for interacting with the endogenous gs-1 mRNA or protein. It seems that the NheI fragment in the antisense orientation (the orientation that it is in pMYX107) is able to form a hairpin loop.

There are alternative tools available for studying the effects of knock-out mutations in yeast and fungi than for higher organisms, and this may be one reason why antisense methodologies have not been more actively pursued in the prior art. Another reason may be the skepticism surrounding antisense studies in fungi because they have not been shown to have the unwinding/modifying enzyme found in mammalian cells used to degrade RNA duplexes. However, as described herein, antisense methodologies have been shown to inhibit fungal growth, and may potentially lead to a new source of antifungal therapeutics.

What is claimed is:

1. Purified DNA encoding (1,3)β-glucan synthase wherein said (1,3)β-glucan synthase has an amino acid sequence of SEQ ID NO:2.

2. Purified DNA comprising a fragment of the sequence of SEQ ID NO: 1 and encoding a protein having (1,3)β-glucan synthase catalytic activity.

3. Purified DNA encoding (1.3)β-glucan synthase and having the sequence of SEQ ID NO:1.

4. An expression vector containing the purified DNA of claim 1.

5. A recombinant host cell containing the expression vector of claim 4.

6. A process for producing a recombinant (1,3)β-glucan synthase, comprising:
   (a) transforming a host cell with the purified DNA of claim 1 to produce a recombinant host cell;
   (b) culturing the recombinant host cell to produce recombinant (1,3)β-glucan synthase; and
   (c) isolating and purifying the (1,3)β-glucan synthase protein.

7. A process for cloning a (1,3)β-glucan synthase gene comprising the steps of:
   (a) generating (1,3)β-glucan synthase mutants from a temperature-sensitive osmotic mutant of Neurospora crassa;

(b) cultivating cell-wall-less (1,3)β-glucan synthase mutants from said (1,3)β-glucan synthase mutants;

(c) preparing pools of cDNA from a Neurospora crassa genomic library, said cDNA being located on a cosmid which has a hygromycin-resistance gene;

(d) transforming the (1,3)β-glucan synthase mutants with the cDNA to form transformants;

(e) identifying the transformants by selecting for the hygromycin-resistance gene on said cosmid; and (f) isolating an individual cosmid that complements said (1,3)β-glucan synthase mutants using a sib selection procedure to yield a cloned (1,3)β-glucan synthase gene.

8. The process of claim 7, wherein the temperature sensitive osmotic mutant of *Neurospora crassa* is obtained by crossing *Neurospora crassa* os-1 (NM233t)A with nic-1(S1413)a.

9. The process of claim 7, wherein the step of generating the (1,3)β-glucan synthase mutants comprises the steps of incubating cells of the temperature sensitive osmotic mutant of *Neurosvora crassa* at a non-permissive temperature until the cells are converted to protoplasts, mutagenizing the protoplasts by ethylmethanesulfonate mutagenesis, and plating the mutagenized protoplasts at a permissive temperature.

10. The process of claim 9, wherein the protoplasts are cultivated in Vogel's medium N supplemented with 7.5% wt/vol sorbitol and 1.5% wt/vol sucrose.

11. The process of claim 9, wherein the non-permissive temperature is about 37° C.

12. The process of claim 11, wherein the permissive temperature is about 25° C.

13. The process of claim 7 wherein said step of preparing pools of cDNA comprises:

(a) obtaining an *E. coli* transformant containing a cDNA from *Neurospora crassa*;

(b) preparing replicated plates of the transformant;

(c) incubating the replicated plates to allow the transformant to reproduce to yield replicated transformants;

(d) transferring the replicated transformants to liquid cultures and incubating further to allow additional reproduction of the replicated transformants; and (e) isolating the cDNA from the replicated transformants.

14. The process of claim 7, wherein the step of preparing pools of cDNA comprises:

(a) placing an *E. coli* DH5αMCR transformant into a microtiter well;

(b) replicating the transformant onto an LB solid medium containing ampicillin to form replicated plates;

(c) incubating the replicated plates at 37° C. for about 12 hours to allow the transformant to reproduce and yield replicated transformants;

(d) scraping the replicated transformants from the replicated plates;

(e) suspending the the replicated transformants in an LB medium containing ampicillin to form liquid cultures;

(f) incubating the cultures at 37° C. at 225 rpm for 2 hours; and (g) isolating the cDNA using a gentle alkaline lysis protocol, lithium chloride precipitation, and centrifugation in CsCl-ethidium bromide gradients.

15. The process of claim 7 wherein the transforming step is performed using a modified Vollmer-Yanofsky procedure, wherein aliquots of the transformation mixture are spread onto plates containing a 7-ml agar-solidified SS medium layer over a 25-ml bottom layer of agar-solidified SS medium supplemented with one of the group consisting of hygromycin at 150 units/ml and benomyl at 250 ng/ml.

16. The process of claim 7 and further comprising the steps of:

(a) digesting the individual cosmid that complements said (1,3)β-glucan synthase mutants with at least one restriction endonuclease to produce a restriction fragment;

(b) cotransforming the restriction fragment with a benomyl-resistant plasmid into the (1,3)β-glucan synthase mutant to yield a restriction fragment-containing transformant; and (c) isolating an individual restriction fragment-containing transformant that complements the (1,3)β-glucan synthase mutants to yield a subcloned (1,3)β-glucan synthase gene.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 2585 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (iv) ANTI-SENSE: NO (vi) ORIGINAL SOURCE:
      (A) ORGANISM: Neurospora crassa
      (B) STRAIN: wild-type 74-DR 23-1VA
      (D) DEVELOPMENTAL STAGE: Mycelial (vii) IMMEDIATE SOURCE:
      (A) LIBRARY: lamda Zap cDNA
      (B) CLONE: gs-1

(viii) POSITION IN GENOME:
      (A) CHROMOSOME/SEGMENT: linkage group V (xi) SEQUENCE DESCRIPTION: SEQ ID NO:1:

```
AAGGGAATAC CCCCCCTTGA ATCTTCGACT CTGGTCCTTT GTCCTCTCCT GTCACCAACG      60

ACGGATTGCA AGACCAGCGC AATTCCTTCT CCCGATTTCG AGCCTCTGAC CGCATACATA     120

TTCTATCTGA TTGCCCAAAA TGGCTGGCTT ATTCAAGGAC ATCTGGCATG CTATGACCAG     180

TTATGATCGA CATGCTGGCA TCGACTCTCC TTACCGAACT GGACGTCATG TCCCATTGAA     240

CCGGAACTCC GGTCTCGCGG GCGTTACTAC CGCCTCCGAC TCGCGTGCCG ACATCAACTC     300

GCCCTACCTT CAAGGAGATG GCCGTGGTTC TACCATGAGC TTCGACACGG CCTACGGTGG     360

ACGCGCCATA TCTCCCATGC CGAGTCCCGC CAACGGTGGC CCCTATTCGC CCGGCCTAGT     420

GAGCCAACGA CAGTCCGTCC ACCAGGACGA ATTCGATGTA CACAGCCCAA CCGGCGAGAT     480

TCCCATGCAG AACTTCCAAA ATGGCGGTCC GCCTCCCCCA CCAGTCGCTA GCTCCTGGGA     540

GAAAATTGAC AGATGGGCCG AGGAAAACTA CCCCGAGTTG TTCGACCAAC TTGGCGAGGG     600

CTGCACCGTC AACGATCTGA ACGAACTCGA ATACCAGCTT GATTGCACCC TTCCCCAAGA     660

TCTCAGGCAA TCCTTGCAAA TCCACGACGG CCAGGAGCGC GGTGGTCTTC CCACTGGCAT     720

TATTTTCAGC TCCATGTTGC TCGACTGCGA AGAGATGGTT CAGGAGTGGG AGAACTGGAA     780

GACGGTGAAC CAAGAGTTTA TGCTGGATCC CGTGCTCGTC AAGCGACAAT CTCAGGCATT     840

TGCCGCTCAG GCCTCATCAT CAAAAGATGC CCCTAACCGC AACCAAAACT GGCGACAAGA     900

ACTTCTCAAC AAGCAGGATT CCGTCCCCCC GGCCGCGATT CAGAAGGCGT ATGCGCACCC     960

TGCCTGGATT CCTCTCGTTC GTGACTGGGG CGGCAACAAC TTGGCTGTCG ATTTGGCGCC    1020

TGGACCAAAG GGCCACTGGG GTCAAATCAT CCTCTTTGGT CGCGACTACG ATACAAAGTA    1080

CGTCGTGGCC CGCTCGTGGG CGCACTTCCT TGCCATGGTT GCCGAGGATC TCAGCAGCGG    1140

GAGGTGGTTT GTCGATGAGG ACACCAACGA GCTCAAGCTG CGTGAGTTTA AGGCGACCCG    1200

TGTTGAGCCG TCTTATTTCG AGATTCTGAG GTGGAGAATG GATCAGAAGT ATGGTCGCAC    1260

AGCCAACAAG CGCAAATCTA TGGCGCCTTC CATGGCGTCA GCTTCCGGCA TGCGCTCTCC    1320

CCCCACTCCC GGCTCTCCCT ACCAAAGCCC AACAGAGCAC AACGAGCCTC GTGGCCGGTC    1380

GCTACACCGT CTCACTGGCA CTTCACCCAT GTCGAGTCCC ATCCGACCAG GTTACGGAAA    1440

GCCAAGCCCA TTGGCGCGCG TTGCTGAGGA GGCACCCCCC ACAACCTCTC TCACGGCTAG    1500

CAACGCCTCC CTCGAGGCCA AAGCCGCCGA CAACTTGATG GAGTTGAACA CCCCAAGGAC    1560

AAGCGGAGAG CATAGCAAGG AGGATATCAA GGTCAATGAG GATTCTCCCG CCAAGGAAAG    1620

GACAAGCGAG GATAAGGAGA AGAAGCCTGA AACCGAGGCG AACGGAAAGG CGACGGAGTC    1680

AAAGGGCAAG CAAACGACAG TCGAAGACGC CGAGGACATG AAGGATATCG AGATTTAAAA    1740

GGGAACAAAT CGAAGCGACC CAACGAACTC GTCAACTCAT GGGTCACCAT TGAGTAGCTG    1800

GCCCAGCAAA CTGCTTCCTC ACCATGCGCA GGGCACGGAG TCAGACAAGG TGTAATGTTT    1860

CTCCCTAATC TGATATCTTG ACGCCTCCTC GAGCCAGTTG TCCTCTCTTG GCCGAATATA    1920

AGGGCCATCG CATGATGAAG GGGCAGGTCA CGAATCTTTG TGTTCCAATT ACTTCTTCCT    1980

CGCCACCATA CGATTAGTCT CTATCGTCTA ATCGGGTTCT TTCATGATGC GGGGGTTTTC    2040

CCTGCGTTGT CCTCTCGCCT GTTTGGCCAA GGAGAGGGGG GTTTTCGAGG ACAATCTCG    2100

TTGCATCGCC GAAGTTTGAA TATTGTATGT ACACTAAAAG GGGATCATTT TGACTTCGAC    2160

TGGTGGGTGG GACCTTGTTG TGGTCTGCCC GACGCCGCCC GCAGAAGACA TTTTCAGCTT    2220

TGCACTATTG TTTACTATTA CACTGCATAG CGTCATAATA ACTCTTTCTG TCTTTATTTT    2280

CTGCATCCAA GCTGTCTTGG CTTCTGGAGG GGAACTGTGG TTACTTACTT CCCCTGGTGC    2340
```

```
TGTCGTTGGC TGGTTGTCAG CCACATGGAA GGAAGTTCAC GCTCGGATGC TGAGTTGGTA    2400

CCGTTGTCAG TGATTTATCG AACTCGGAAG GCGCTGATTT TTTTTTTAAA GTTCGGACTG    2460

TTATTAGGGG GAGTTCGAAG AGGGTGGTCG AGGGAACAAG TGCTTTGTAT TTACATGGGA    2520

AGGGTATAGA CATGGATGGT AGGGAGAGAA TCAACAAAGC GTAAAAACAA AAAAAAAAA     2580

AAAAA                                                                2585
```

(2) INFORMATION FOR SEQ ID NO:2:

(i) SEQUENCE CHARACTERISTICS:
        (A) LENGTH: 532 amino acids
        (B) TYPE: amino acid
        (C) STRANDEDNESS: Not Relevant
        (D) TOPOLOGY: Not Relevant (ii) MOLECULE TYPE: protein (iii) HYPOTHETICAL: NO (iv) ANTI-SENSE: NO (vi) ORIGINAL SOURCE:
        (A) ORGANISM: Neurospora crassa
        (B) STRAIN: wild-type 74-DR 23-1VA
        (D) DEVELOPMENTAL STAGE: Mycelial (xi) SEQUENCE DESCRIPTION: SEQ ID NO:2:

```
Met Ala Gly Leu Phe Lys Asp Ile Trp His Ala Met Thr Ser Tyr Asp
1               5                   10                  15

Arg His Ala Gly Ile Asp Ser Pro Tyr Arg Thr Gly Arg His Val Pro
            20                  25                  30

Leu Asn Arg Asn Ser Gly Leu Ala Gly Val Thr Ala Ser Asp Ser
        35                  40                  45

Arg Ala Asp Ile Asn Ser Pro Tyr Leu Gln Gly Asp Gly Arg Gly Ser
    50                  55                  60

Thr Met Ser Phe Asp Thr Ala Tyr Gly Gly Arg Ala Ile Ser Pro Met
65                  70                  75                  80

Pro Ser Pro Ala Asn Gly Gly Pro Tyr Ser Pro Gly Leu Val Ser Gln
                85                  90                  95

Arg Gln Ser Val His Gln Asp Ala Phe Asp Val His Ser Pro Thr Gly
            100                 105                 110

Glu Ile Pro Met Gln Asn Phe Gln Asn Gly Gly Pro Pro Pro Pro
        115                 120                 125

Val Ala Ser Ser Trp Glu Lys Ile Asp Arg Trp Ala Glu Glu Asn Tyr
    130                 135                 140

Pro Glu Leu Phe Asp Gln Leu Gly Glu Gly Cys Thr Val Asn Asp Leu
145                 150                 155                 160

Asn Glu Leu Glu Tyr Gln Leu Asp Cys Thr Leu Pro Gln Asp Leu Arg
                165                 170                 175

Gln Ser Leu Gln Ile His Asp Gly Gln Glu Arg Gly Gly Leu Pro Thr
            180                 185                 190

Gly Ile Ile Phe Ser Ser Met Leu Leu Asp Cys Glu Glu Met Val Gln
        195                 200                 205

Glu Trp Glu Asn Trp Lys Thr Val Asn Gln Glu Phe Met Leu Asp Pro
    210                 215                 220

Val Leu Val Lys Arg Gln Ser Gln Ala Phe Ala Ala Gln Ala Ser Ser
225                 230                 235                 240

Ser Lys Asp Ala Pro Asn Arg Asn Gln Asn Trp Arg Gln Glu Leu Leu
                245                 250                 255
```

```
        Asn Lys Gln Asp Ser Val Pro Pro Ala Ala Ile Gln Lys Ala Tyr Ala
                    260                 265                 270

His Pro Ala Trp Ile Pro Leu Val Arg Asp Trp Gly Gly Asn Asn Leu
                275                 280                 285

Ala Val Asp Leu Ala Pro Gly Pro Lys Gly His Trp Gly Gln Ile Ile
            290                 295                 300

Leu Phe Gly Arg Asp Tyr Asp Thr Lys Tyr Val Val Ala Arg Ser Trp
        305                 310                 315                 320

Ala His Phe Leu Ala Met Val Ala Glu Asp Leu Ser Ser Gly Arg Trp
                        325                 330                 335

Phe Val Asp Glu Asp Thr Asn Glu Leu Lys Leu Arg Glu Phe Lys Ala
                    340                 345                 350

Thr Arg Val Glu Pro Ser Tyr Phe Glu Ile Leu Arg Trp Arg Met Asp
                355                 360                 365

Gln Lys Tyr Gly Arg Thr Ala Asn Lys Arg Lys Ser Met Ala Pro Ser
            370                 375                 380

Met Ala Ser Ala Ser Gly Met Arg Ser Pro Thr Pro Gly Ser Pro
        385                 390                 395                 400

Tyr Gln Ser Pro Thr Glu His Asn Glu Pro Arg Gly Arg Ser Leu His
                    405                 410                 415

Arg Leu Thr Gly Thr Ser Pro Met Ser Ser Pro Ile Arg Pro Gly Tyr
                420                 425                 430

Gly Lys Pro Ser Pro Leu Ala Arg Val Ala Glu Glu Ala Pro Pro Thr
            435                 440                 445

Thr Ser Leu Thr Ala Ser Asn Ala Ser Leu Glu Ala Lys Ala Ala Asp
        450                 455                 460

Asn Leu Met Glu Leu Asn Thr Pro Arg Thr Ser Gly Glu His Ser Lys
        465                 470                 475                 480

Glu Asp Ile Lys Val Asn Glu Asp Ser Pro Ala Lys Glu Arg Thr Ser
                    485                 490                 495

Glu Asp Lys Glu Lys Pro Glu Thr Glu Ala Asn Gly Lys Ala Thr
                500                 505                 510

Glu Ser Lys Gly Lys Gln Thr Thr Val Glu Asp Ala Glu Asp Met Lys
            515                 520                 525

Asp Ile Glu Ile
            530

(2) INFORMATION FOR SEQ ID NO:3:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Neurospora crasssa
        (B) STRAIN: wild-type 74-DR 23-1VA
        (D) DEVELOPMENTAL STAGE: mycelial (vii) IMMEDIATE SOURCE:
        (A) LIBRARY: lamda Zap cDNA
        (B) CLONE: gs-1

(xi) SEQUENCE DESCRIPTION: SEQ ID NO:3:
```

-continued

CAAAATGGCT                                                                      10

(2) INFORMATION FOR SEQ ID NO:4:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer sequence"

(iii) HYPOTHETICAL: NO (iv) ANTI-SENSE: NO (xi) SEQUENCE DESCRIPTION: SEQ ID NO:4:

GAAGAGGGGG GGTCTCGCCC ATTAATCC                                                  28

(2) INFORMATION FOR SEQ ID NO:5:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "reverse primer sequence"

(iii) HYPOTHETICAL: NO (iv) ANTI-SENSE: NO (xi) SEQUENCE DESCRIPTION: SEQ ID NO:5:

ATCCGACCAG GTTACGGAAA GCCAAGCC                                                  28

(2) INFORMATION FOR SEQ ID NO:6:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "reverse PCR primer"

(iii) HYPOTHETICAL: NO (iv) ANTI-SENSE: NO (xi) SEQUENCE DESCRIPTION: SEQ ID NO:6:

ATCCGACCAG GTTACGGAAA GCCAAGCAGC C                                              31